(12) United States Patent
Cheng

(10) Patent No.: US 7,160,315 B2
(45) Date of Patent: Jan. 9, 2007

(54) HANDHELD THERMAL THERAPY DEVICE

(76) Inventor: Tzu-Chen Cheng, Av.27 de Febrero, #418, Mirador Norte, La Feria, P.O. Box 165-2, Santo Domingo, D.N. (DO)

( * ) Notice: Subject to any disclaimer, the term of this patent is extended or adjusted under 35 U.S.C. 154(b) by 0 days.

(21) Appl. No.: 11/263,909

(22) Filed: Nov. 2, 2005

(65) Prior Publication Data

US 2006/0060184 A1    Mar. 23, 2006

Related U.S. Application Data

(63) Continuation-in-part of application No. 10/347,101, filed on Jan. 17, 2003.

(51) Int. Cl.
*A61F 7/00* (2006.01)
(52) U.S. Cl. .................................. 607/96; 601/15
(58) Field of Classification Search .................. 604/24; 607/96; 601/15
See application file for complete search history.

(56) References Cited

U.S. PATENT DOCUMENTS

| | | | | |
|---|---|---|---|---|
| 1,817,823 A | * | 8/1931 | Ito .............................. | 604/24 |
| 1,831,669 A | * | 11/1931 | Kono .......................... | 604/24 |
| 4,090,517 A | * | 5/1978 | Takenaka .................... | 604/114 |
| 4,203,438 A | * | 5/1980 | Shiu ............................ | 604/24 |
| 4,604,088 A | * | 8/1986 | Nottbohm .................... | 604/24 |
| 4,671,788 A | * | 6/1987 | Wu .............................. | 604/24 |
| 4,731,050 A | * | 3/1988 | Harada et al. ................ | 604/24 |
| 5,549,960 A | * | 8/1996 | Yoo ............................ | 428/139 |
| 5,632,768 A | * | 5/1997 | Shimada ..................... | 607/96 |
| 5,904,664 A | * | 5/1999 | Kim ............................ | 604/19 |
| 5,931,806 A | * | 8/1999 | Shimada ..................... | 604/24 |
| 6,764,454 B1 | * | 7/2004 | Tu .............................. | 601/15 |

* cited by examiner

*Primary Examiner*—Henry M Johnson, III
(74) *Attorney, Agent, or Firm*—Leong C. Lei

(57) ABSTRACT

A thermal therapy device mainly contains a handle member, a burning member, and an ashes storage member, cascaded together into a rod-like heat source suitable for hand gripping. A ventilating section is configured between the handle member and the burning member surrounded by an anti-leaking ring. A supporting member is installed inside the burning member to hold a fuel bar. A portion of heat produced by the burning of the fuel bar radiates to the wall of the burning member while another portion of the heat is stored in a heat storage element of the supporting member surround by a thicker wall of the burning member so that the heat could be maintained for an extended period of time. The ashes storage member is at the bottom of the device to collect the ashes from the burning of the fuel bar. The ashes storage member has an axial through hole for smooth air circulation.

5 Claims, 5 Drawing Sheets

HANDHELD THERMAL THERAPY DEVICE

This application is a continuation-in-part of the pending patent application Ser. No. 10/347,101 filed Jan. 17, 2003.

BACKGROUND OF THE INVENTION (a) Technical Field of the Invention

The present invention generally relates to thermal therapy devices, and more particularly to a handheld thermal therapy device using internal burning to produce heat.

(b) Description of the Prior Art

Thermal treatment is a common therapy practice in which a heat source is applied to human body so that the heat is conducted to the muscle via skin tissues to relieve sore and pain, or to improve local blood circulation.

Thermal treatment could be conducted using various kinds of heat sources such as hot towels, thermal pads using chemicals, electrical heaters, or even torches. One popular thermal therapy device is a portable one with an internal burning mechanism that could be used without time and place limitations. FIG. 1 is a perspective view showing the various parts of such a conventional thermal therapy device. As illustrated, the thermal therapy device 1 mainly contains a lower tubular member 11, an upper tubular member 12, a spring 13, and a push rod 14.

The lower tubular member 11 contains a lower section 111 and an upper section 112 which are screwed together. The lower part of the lower section 111 is configured with bulges with elongated openings.

The upper tubular member 12 also contains a lower section 121 and an upper section 122 which are screwed together. In the middle of the lower section 121, an oval-shaped indentation is configured having an opening at its lower part covered by an extended blade.

The push rod 14 is installed inside the upper tubular member 12 which, in turn, is threaded through the spring 13 and inserted into the lower tubular member 11. When in use, a burnable fuel source is fixed between the oval-shaped indentation and the extended blade, and is ignited. As the fuel source is burned, the heat produced is conducted to the human body via the wall of the lower tubular member 11. This conventional design has a number of disadvantages. For example, the air circulation is usually poorly designed and the burning of the fuel source as such is easily extinguished. The conventional device also has no heat storage capacity and the produced heat is dissipated too quickly when used in an environment with strong air flow.

SUMMARY OF THE INVENTION

The primary purpose of the present invention is to provide a novel thermal therapy device herein which obviate the disadvantages of conventional devices.

The thermal therapy device mainly contains a handle member, a burning member, and an ashes storage member, cascaded together into a rod-like heat source suitable for hand gripping. A ventilating section is configured between the handle member and the burning member, which is surrounded by an anti-leaking ring so that the handle member wouldn't get too hot to hold and the fuel from the burning member wouldn't leak outside of the device. A supporting member is installed inside the burning member to hold a burnable fuel bar. A portion of heat produced by the burning of the fuel bar radiates to the wall of the burning member while another portion of the heat is stored in a heat storage element of the supporting member. A thicker wall of the burning member surrounds the heat storage element so that the produced heat could be stored and maintained for an extended period of time. The ashes storage member is at the bottom of the device to collect the ashes from the burning of the fuel bar. The ashes storage member has an axial through hole for smooth air circulation.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
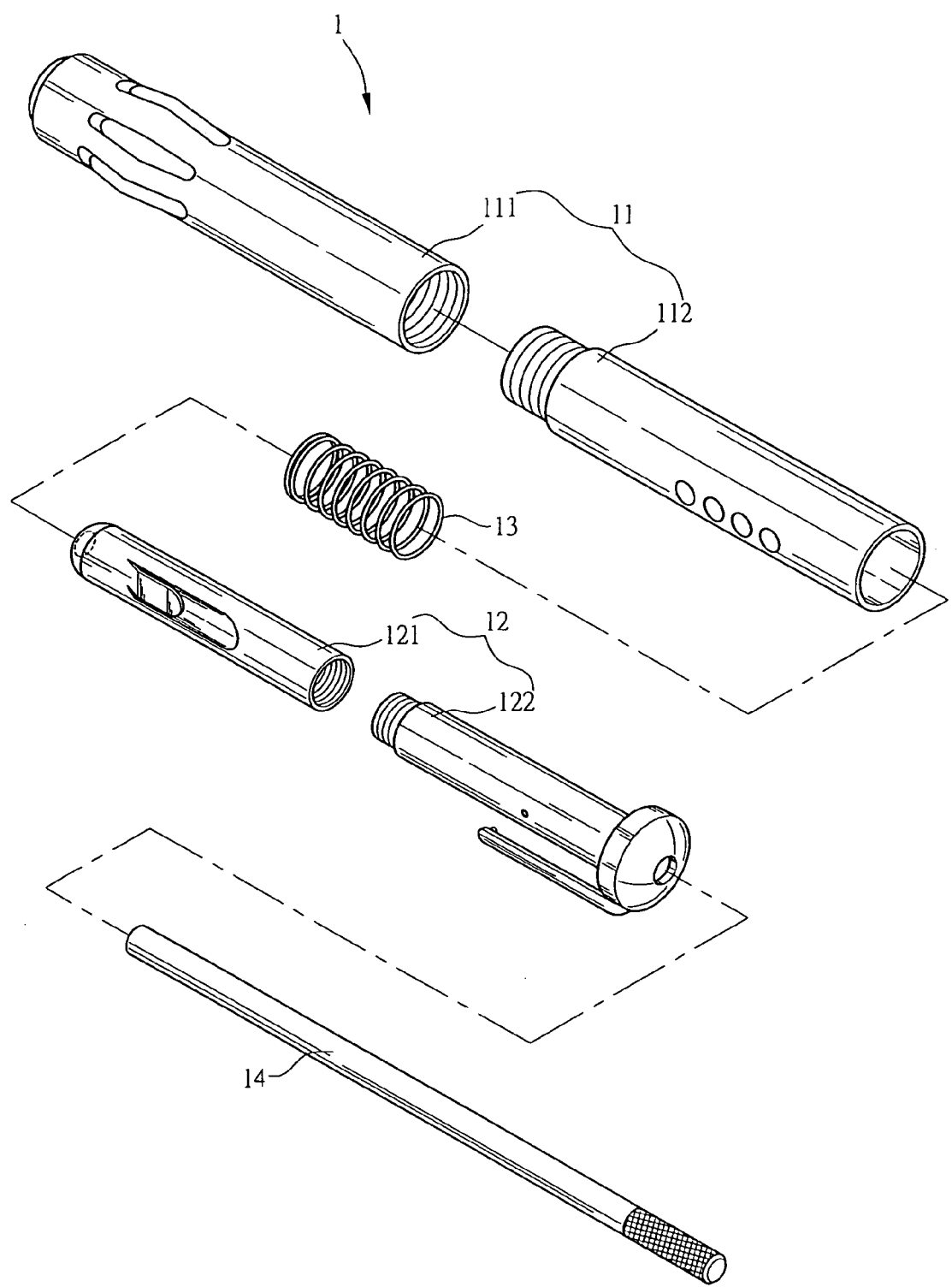
FIG. 1 is a perspective view showing the various parts of a conventional thermal therapy device.
Figure 2:
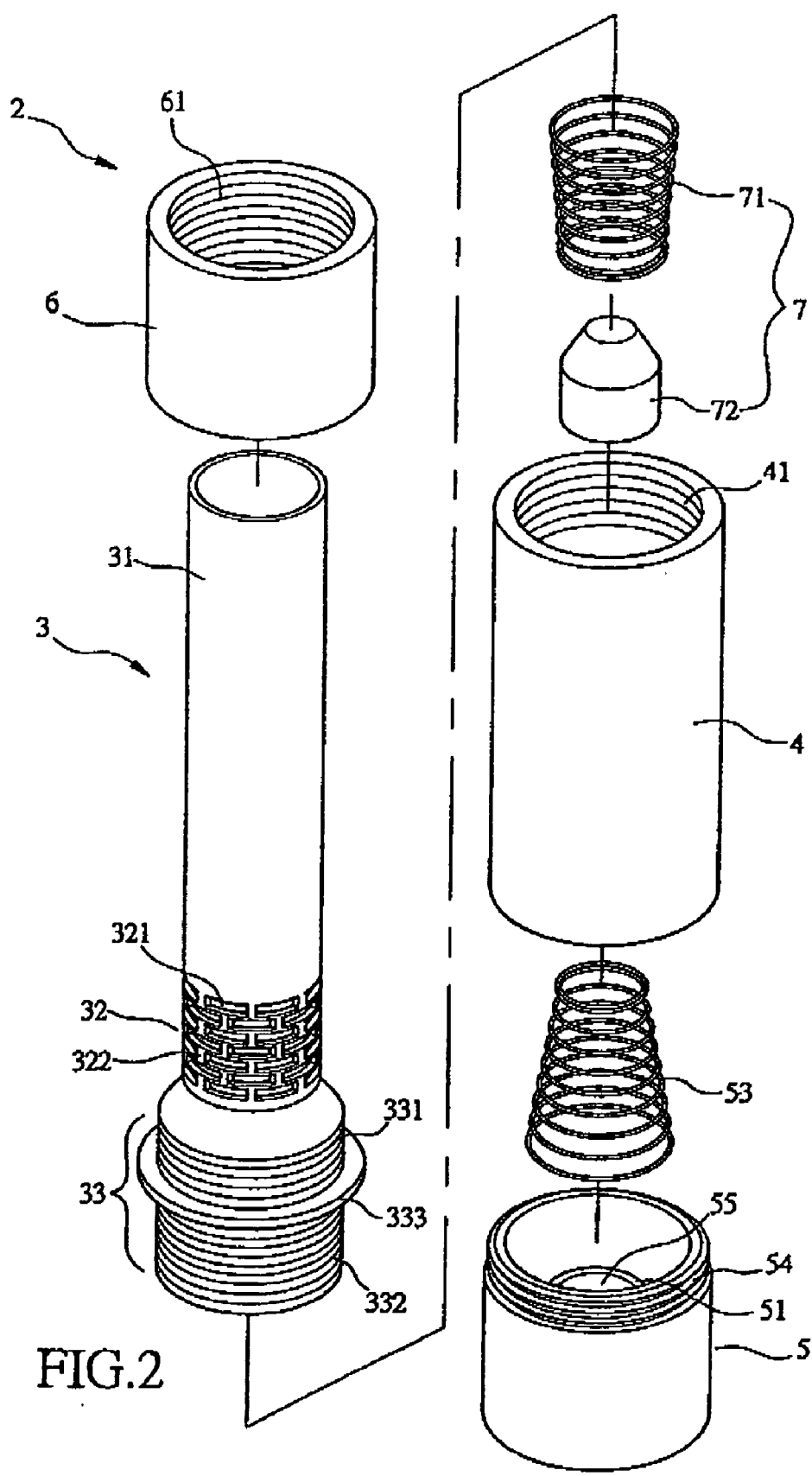
FIG. 2 is a perspective view showing the various parts of a thermal therapy device according to an embodiment of the present invention.
Figure 3:
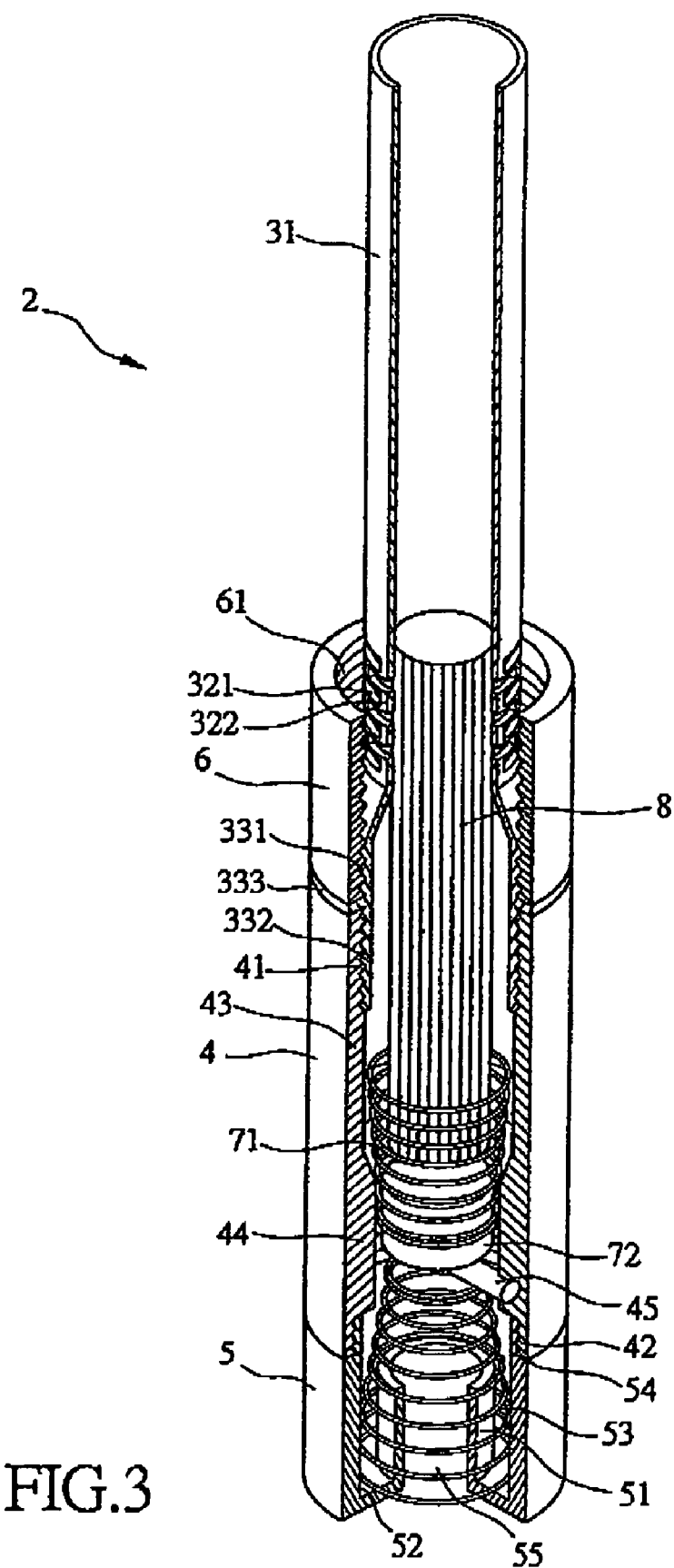
FIG. 3 is a perspective transparent view showing the thermal therapy device of FIG. 2 after it is assembled.
Figure 4:
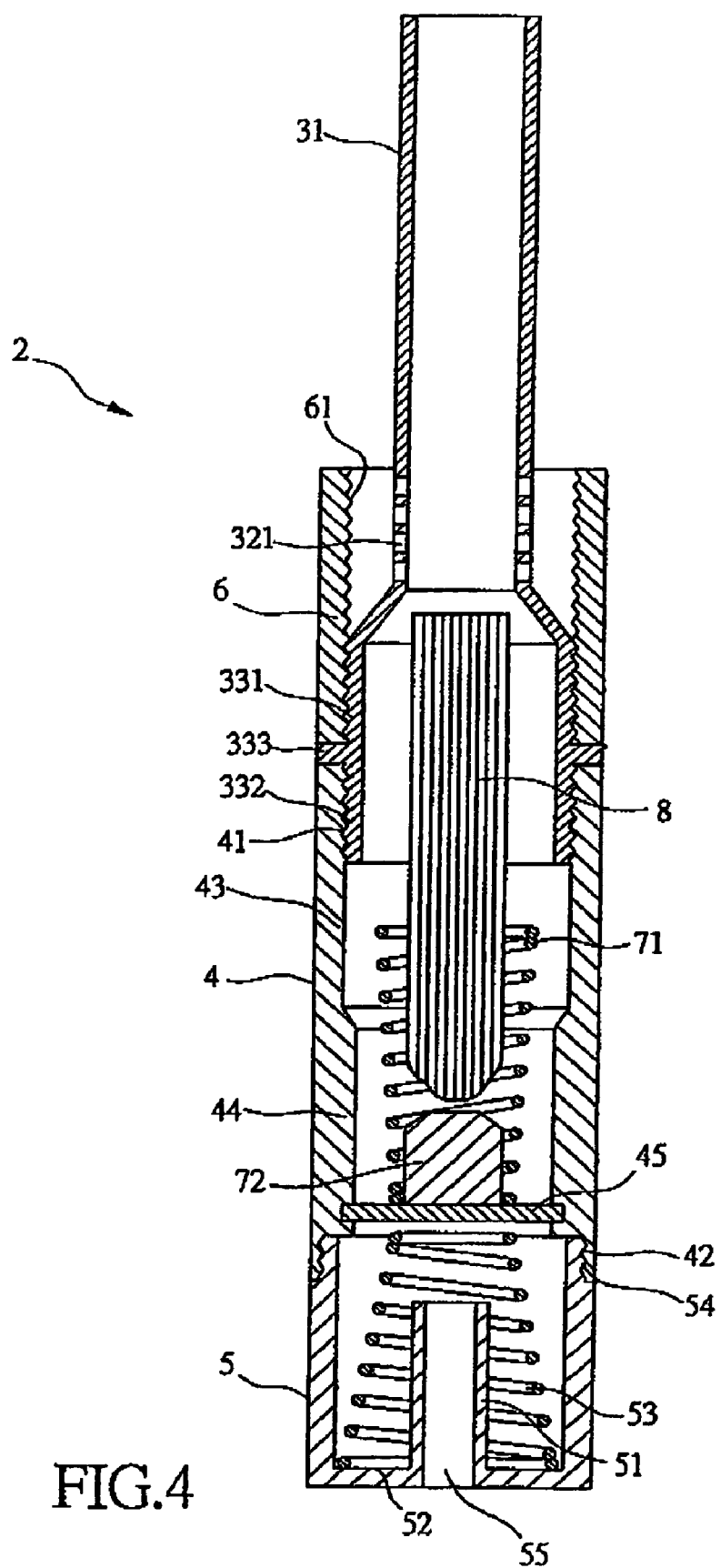
FIG. 4 is a sectional view showing the thermal therapy device of FIG. 2 after it is assembled.

As shown in FIGS. 2~4, a thermal therapy device 2 according to an embodiment of the present invention mainly contains a handle member 3, a burning chamber 4, and an ashes storage member 5.

The handle member 3 is a hollow tube having a holding section 31 with smooth surface for the gripping by a user's hand. At an end of the handle member 3, there is a fastening section 33 with encircling screw threads. A flange 333 in the middle of the fastening section 33 divides the fastening section 33 and the screw threads into an upper (i.e., closer to the holding section 31) fastening section 331 and a lower (i.e., farther from the holding section 31) fastening section 332. The upper fastening section 331 is for screwing an anti-leaking ring 6 onto the handle member 3. The lower fastening section 332 is for screwing the burning chamber 4 onto the handle member 3. Between the holding section 31 and the fastening section 33, a ventilating section 32 is configured, which contains a number of through holes 321 separated by bars 322 along the axial direction. The through holes 321 are distributed round the circumference of the ventilating section 32 into a number of layers. The through holes 321 of the adjacent layers are arranged such that the bars 322 are interleaved (i.e., not aligned). The through holes 321 allow the exchange of the exhaust produced by the burning chamber 4 and outside cool air, and prevent the heat from the burning chamber 4 from conduction to the handle member 3.

The burning chamber 4 is also a hollow tube which has upper and lower screw threads 41 and 42 configured on the inside walls of its two ends. The upper screw thread 41 corresponds to the screw thread of the lower fastening section 332 and is for the joining of the burning chamber 4 to the handle member 3. The lower screw thread 42 is for screwing the ashes storage member 5 onto the burning chamber 4. Inside the burning chamber 4 and above the lower screw thread 42, a heat conduction rod 45 is configured diametrically across the aperture of the burning chamber 4. The heat conduction rod 45 confines a supporting member 7 inside the burning chamber 4. The supporting member 7 contains a heat storage element 72 and an elastic element 71 which surrounds the heat storage element 72 at the bottom and supports a fuel bar 8 at the top. Please note that the burning chamber 4 has a thicker wall 44 at its lower section than the thinner wall 43 at the upper section. The thicker wall 44 surrounds the heat storage element 72 so that the heat produced by the burning chamber 4 wouldn't get lost quickly.

The ashes storage member 5 is also a hollow tube with an inner tube 51 extended from the lower end of the storage member 5 upward for an appropriate distance. The ashes storage member 5 has a screw thread 54 configured on the outside wall of its upper end. The screw thread 54 corresponds to the lower screw tread 42 and is for the joining of the ashes storage member 5 to the burning chamber 4. The gap between the inner tube 51 and the outer tube (not numbered) are closed at the lower end of the ashes storage member 5, which thereby forms an ashes storage section 52. The aperture 55 of the inner tube 51 functions as the ventilation hole allowing air to flow into the inside of the burning chamber 4 to support the burning of the fuel bar 8. The inner tube 51 is surrounded by an ashes collection element 53 so that ashes from the burning chamber 4 would be collected into the ashes storage section 52.

To use the present embodiment, a user first joins the ashes storage member 5 with the burning chamber 4. The supporting member 7 is then placed inside the burning chamber 4. Subsequently, the user ignites the fuel bar 8 and lets the supporting member 7 to hold the fuel bar 8. The handle member 3 is then joined with the burning chamber 4. The anti-leaking ring 6, in turn, is locked to the upper fastening section 331 of the handle member 3. The present embodiment is now ready for use.

Figure 5:
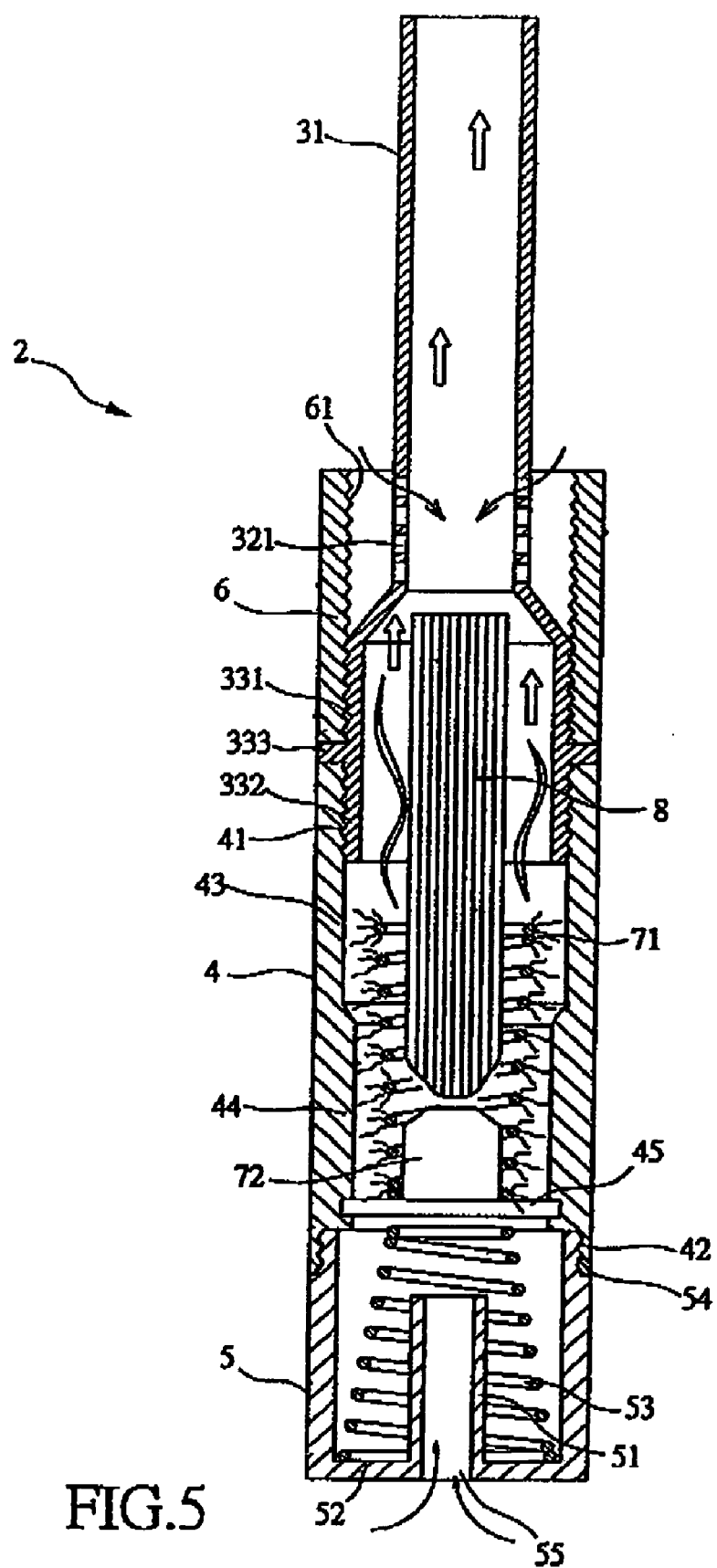
FIG. 5 is a sectional view showing the air flow of the thermal therapy device of FIG. 2 when it is operated.

As shown in FIG. 5, when the fuel bar 8 is burning inside the burning chamber 4, a portion of the heat produced is radiated to the wall of the burning chamber 4. Another portion of the heat produced is absorbed by the heat storage element 72 and then conducted to the wall of the burning chamber 4 by the heat conduction rod 45. The ashes resulting from the burning of the fuel bar 8 falls downward freely and, through the collection of the ashes collection element 53, into the ashes storage section 52 of the ashes storage member 5.

When the temperature around the outside of the burning chamber 4 has reached an appropriate level for healing and therapy, the user could grasp the holding section 31 of the handle member 3 and make the outside of the burning chamber 4 to contact body parts to relieve pains.

A benefit of the present invention lies in that a smooth air circulation is provided by allowing outside fresh air to flow into the burning chamber 4 via the aperture 55 of the ashes storage member 5, to rise up as the air is heated along the handle member 3, and to flow out from the top of the handle member 3. As such, a steady burning of the fuel bar 8 is maintained. Similarly, the exhaust produced by the burning chamber 4 is also expelled through the same route. The configuration of the ventilating section 32 prevents the heat from conduction from the burning chamber 4 to the handle member 3. In addition, additional cool air is introduced into the handle member 3 via the ventilating section 32 to improve the efficiency of eliminating the exhaust. On the other hand, the configuration of the anti-leaking ring 6 prevents oil produced by the fuel bar 8 from flowing to the burning chamber 4 to pollute the user's body. The present invention is therefore safer and cleaner to use.

Another benefit of the present invention is that, by having a heat storage element 72 and a thicker wall 44 surrounding the heat storage element 72, the heat produced by the burning chamber 4 could be maintained for an extended period of time.

To achieve the maximum effect, the various parts of the thermal therapy device 2 of the present invention are best implemented using ceramic or metallic materials. Preferably, stainless steel should be used.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A thermal therapy device comprising:
a hollow handle having an end provided with a fastening section with screw threads, said fastening section having an intermediate portion formed with a flange which divides said fastening section into an upper fastening section and a lower fastening section, said handle having a ventilation section above said upper fastening section;
an anti-leaking ring threadedly engaged with said upper fastening section;
an ashes storage member being a hollow tube with an inner tube extended upwardly from a lower end of said ash storage member to form an ashes storage section between an inner wall of said hollow tube and an outer wall of said inner tube;
an ashes collection element fitted over said inner tube; and
a burning chamber being a hollow cylinder having an end threadedly engaged with said ash storage member and a second end threadedly engaged with said lower fastening section, said hollow cylinder having an outer wall of increased thickness near said ash storage member and further comprising a supporting member within the cylinder, said supporting member including a heat storage element and an elastic coil element wherein a fuel bar is supported longitudinally by the heat storage element and laterally by the elastic coil element.

2. The thermal therapy device as claimed in claim 1, wherein said ventilating section comprises a plurality of through holes separated by a plurality of bars, and said through holes are distributed around a circumference of said handle member into a plurality of layers.

3. The thermal therapy device as claimed in claim 2, wherein said through holes are configured such that said bars at adjacent layers are interleaved.

4. The thermal therapy device as claimed in claim 1, wherein said burning chamber has a heat conduction rod positioned under said supporting member.

5. The thermal therapy device as claimed in claim 1, wherein said inner tube of said ashes storage member is open at both ends.

* * * * *